(12) United States Patent
Dong et al.

(10) Patent No.: US 8,488,122 B2
(45) Date of Patent: Jul. 16, 2013

(54) TURBIDITY SENSORS AND PROBES

(75) Inventors: Guoquan Dong, Beavercreek, OH (US); Daniel L. Lauchner, Englewood, OH (US)

(73) Assignee: YSI Incorporated, Yellow Springs, OH (US)

( * ) Notice: Subject to any disclaimer, the term of this patent is extended or adjusted under 35 U.S.C. 154(b) by 164 days.

(21) Appl. No.: 13/033,103

(22) Filed: Feb. 23, 2011

(65) Prior Publication Data

US 2011/0273710 A1    Nov. 10, 2011

(51) Int. Cl.
*G01N 21/55* (2006.01)

(52) U.S. Cl.
CPC ................................... *G01N 21/55* (2013.01)
USPC .................................................... 356/445

(58) Field of Classification Search
CPC ..................................................... G01N 21/55
USPC .................................... 356/445–448
See application file for complete search history.

(56) References Cited

U.S. PATENT DOCUMENTS

| | | | |
|---|---|---|---|
| 5,235,526 A | 8/1993 | Saffell | |
| 5,350,922 A | 9/1994 | Bartz | |
| 5,440,126 A * | 8/1995 | Kemsley | 250/339.12 |
| 5,539,396 A | 7/1996 | Mori et al. | |
| 5,821,405 A | 10/1998 | Dickey et al. | |
| 6,111,249 A | 8/2000 | Garner, III | |
| 6,173,600 B1 | 1/2001 | Harada et al. | |
| 6,305,944 B1 | 10/2001 | Henry et al. | |
| 6,405,581 B1 | 6/2002 | Bruhn | |
| 6,535,283 B1 * | 3/2003 | Heffels et al. | 356/300 |
| 6,677,861 B1 | 1/2004 | Henry et al. | |
| 6,678,045 B2 | 1/2004 | Rettig et al. | |
| 6,717,302 B2 | 4/2004 | Kolloff et al. | |
| 6,779,383 B2 | 8/2004 | Lizotte et al. | |
| 6,798,347 B2 | 9/2004 | Henry et al. | |
| 6,842,243 B2 | 1/2005 | Tokhtuev et al. | |
| 6,894,778 B2 | 5/2005 | Palumbo et al. | |
| 6,928,864 B1 | 8/2005 | Henry et al. | |
| 6,938,506 B2 | 9/2005 | Henry et al. | |

(Continued)

FOREIGN PATENT DOCUMENTS

| | | |
|---|---|---|
| DE | 2416939 | 10/1975 |
| EP | 2133687 | 12/2009 |

(Continued)

OTHER PUBLICATIONS

PCT, International Search Report and Written Opinion, International Application No. PCT/US2011/032955 (Oct. 10, 2011).

(Continued)

*Primary Examiner* — Michael P Stafira
(74) *Attorney, Agent, or Firm* — Thompson Hine L.L.P.

(57) ABSTRACT

Turbidity heads for a turbidity sensor or probe and the resulting sensor are disclosed that include a light source providing an outgoing light ray, a photodetector capable of detecting an incoming light ray; an isolator separating the light source from the detector portion; and a first reflector in the path of either the outgoing light ray or the incoming light ray. The first reflector is positioned to reflect either the outgoing light ray or the incoming light ray to achieve a measurement angle defined between the outgoing light ray and the incoming light ray of ninety degrees plus-or-minus two and a half degrees to comply with the standard ISO 7027 for turbidity measurement.

20 Claims, 5 Drawing Sheets

U.S. PATENT DOCUMENTS

| | | | |
|---|---|---|---|
| 6,999,898 B2 | 2/2006 | King et al. | |
| 7,007,541 B2 | 3/2006 | Henry et al. | |
| 7,138,926 B2 | 11/2006 | Henry et al. | |
| 7,142,299 B2 | 11/2006 | Tokhtuev et al. | |
| 7,215,420 B2 * | 5/2007 | Gellerman et al. | 356/301 |
| 7,339,671 B2 | 3/2008 | Peng | |
| 7,832,295 B2 | 11/2010 | Rodriguez et al. | |
| 2001/0055116 A1 * | 12/2001 | Maczura et al. | 356/326 |
| 2003/0117623 A1 * | 6/2003 | Tokhtuev et al. | 356/338 |
| 2004/0130714 A1 * | 7/2004 | Gellerman et al. | 356/300 |
| 2011/0023586 A1 | 2/2011 | Leyer et al. | |

FOREIGN PATENT DOCUMENTS

| | | |
|---|---|---|
| JP | 06-160279 | 6/1994 |
| JP | 2004-117325 | 4/2004 |
| WO | 2009/111090 | 9/2009 |

OTHER PUBLICATIONS

Excerpts from "6000 UPG Multi-Parameter Water Quality Monitor Instruction Manuel," YSI Incorporated (34 pages) (Apr. 1997).

Excerpts from "DataSonde® 4 and Minisonde® Water Quality Multiprobes User's Manual," Hydrolab Corporation (3 pages) (Apr. 1998).

"Field Operation Guide YSI 610 Display/Logger," YSI Incorporated (Aug. 1998).

* cited by examiner

US 8,488,122 B2

TURBIDITY SENSORS AND PROBES

TECHNICAL FIELD

The present application relates to turbidity sensors and probes, in particular, the configuration of turbidity probe heads for probes connectable to sondes.

BACKGROUND

Various water quality monitoring probes have been developed that are connectable to various water quality monitoring instruments including sondes. The probes typically include a sensor for monitoring a parameter such as a parameters of the environment surrounding the instrument. Probes may monitor pH, temperature, turbidity, dissolved oxygen, conductivity, etc.

Turbidity sensing provides a quick, practical indication of the relative amount of suspended solids in water or liquid solutions. Such sensors may be used to measure turbidity of natural water sources, in-situ, for environmental monitoring.

SUMMARY

In one aspect turbidity heads for turbidity sensors or probes are disclosed. The turbidity heads include a light source providing an outgoing light ray, a photodetector capable of detecting an incoming light ray, an isolator separating the light source from the detector portion, and a first reflector in the path of either the outgoing light ray or the incoming light ray. The first reflector is positioned to reflect either the outgoing light ray or the incoming light ray to achieve a measurement angle defined between the outgoing light ray and the incoming light ray of ninety degrees plus-or-minus two and a half degrees to comply with the standard ISO 7027 for turbidity measurement.

In one embodiment, the first reflector is positioned to reflect the outgoing light ray and a second reflector is present that is positioned to reflect the incoming light ray.

The turbidity heads may be packaged in a housing that has a maximum diameter of about 13 mm. This compact arrangement, which includes the light source, photodetector and at least one reflector, is possible because of how the reflector changes the position of the light source and/or photodetector.

In one embodiment, the first reflector may include a prism, a reflective film, a reflective coating, and combinations thereof. If the first reflector is a prism it includes one reflective side. In one embodiment, the prism is a parallelepiped prism.

In another embodiment, the turbidity heads include a first reflector positioned to reflect the outgoing light ray and a second reflector positioned to reflect the incoming light ray. The first and second reflectors may be or include a prism, a reflective film, a reflective coating, and combinations thereof.

In another aspect, turbidity sensors are disclosed that have a watertight housing that houses a light source providing an outgoing light ray, a detector capable of detecting an incoming light ray, an isolator separating the light source from the detector portion, a first reflector in the path of either the outgoing light ray or the incoming light ray, and a circuit board electrically coupled to the light source and the detector. The first reflector is positioned to reflect either the outgoing light ray or the incoming light ray to achieve a measurement angle defined between the outgoing light ray and the incoming light ray of ninety degrees plus-or-minus two and a half degrees.

In one embodiment, the turbidity sensor includes an electrical connector electrically coupled to the circuit board. The electrical connector is capable of electrically coupling the circuit board to a water monitoring device. In one embodiment, the electrical connector is a wet mateable connector. In one embodiment, the water monitoring device is a sonde.

DETAILED DESCRIPTION

Figure 1:
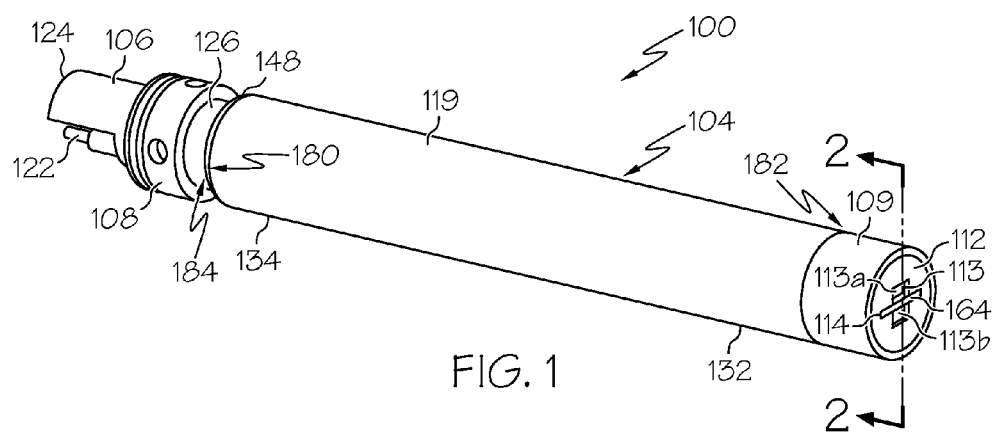
FIG. 1 is a side, perspective view of a turbidity probe.

The following detailed description will illustrate the general principles of the invention, examples of which are additionally illustrated in the accompanying drawings. In the drawings, like reference numbers indicate identical or functionally similar elements.

The term "light" as used herein includes visible light, ultraviolet light, and infrared light.

Figure 2:
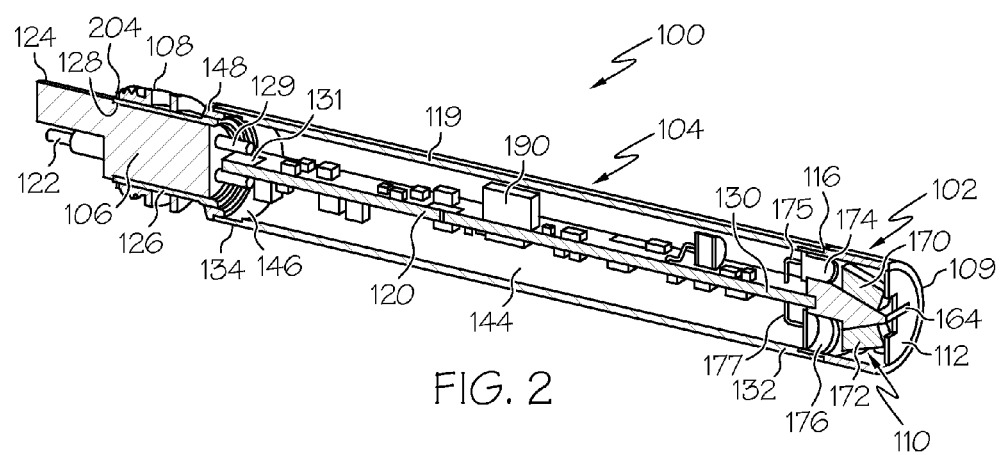
FIG. 2 is a side, cross-sectional, perspective view of the turbidity probe of FIG. 1 taken along line 2-2.

Referring to FIGS. 1-2, a probe, generally designated 100, is shown that includes a turbidity head 102 and a probe body 104 connected together by a second weld 182 to form a watertight assembly. The probe body 104 includes a housing 119 having a distal end 132 and a proximal end 134 which has a circuit board 120 therein, as seen in the cross-section of FIG. 2. The circuit board 120 is electrically connected to an electrical connector 106 that protrudes from the proximal end 134 of the housing 119. The presence of the circuit board 120 within the probe itself makes the probe 100 a "smart probe." Since the probes are often submerged in a fluid sample or fluid environment to monitor a parameter thereof, the housing 119 needs to be "water-tight" to protect the circuit board 120 and other electrical components from water or other fluids. Accordingly, the proximal end 134 of the housing has a first weld 180 to a reducing ring 148 and then a third weld connecting the reducing ring 148 to a casing 126 on the electrical connector 106 to form a water-tight seal between the housing 119 and the casing 126 on the electrical connector 106.

Figure 9:
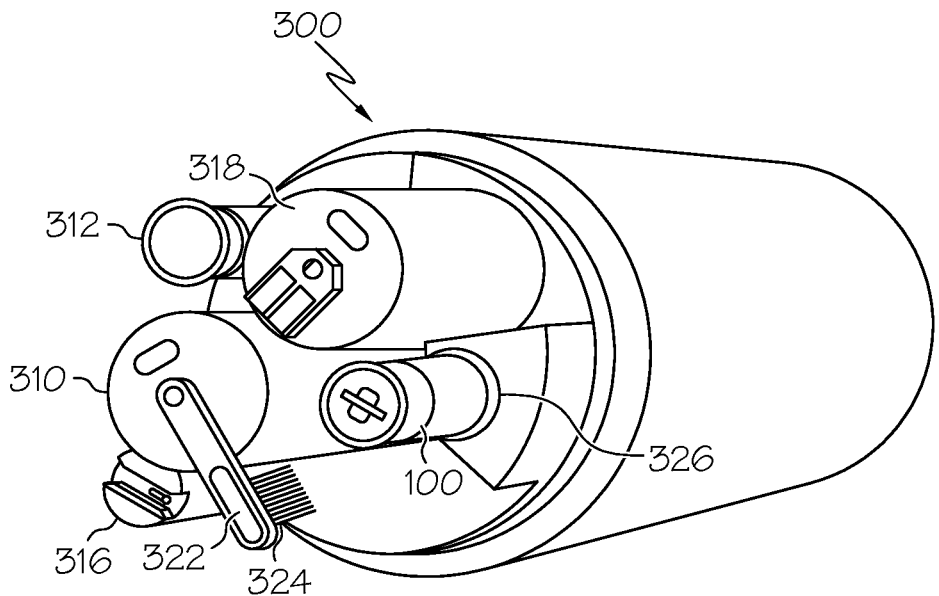
FIG. 9 is a top, perspective view of a sonde that includes at least one turbidity probe.

Probe 100 is connectable to a water monitoring device, for example, a sonde such as the sonde 300 shown in FIG. 9. The probe 100 is electrically connectable to a port 326 of the sonde using the electrical connector 106. The sonde may have a plurality of identical ports for receiving any number of probes capable of detecting various parameters that have the same electrical connector 106. In another embodiment, as shown in FIG. 9, the ports may be of varying sizes.

As best seen in FIGS. 1-2, the electrical connector 106 may include a connecting collar 108 slideably received on a casing 126 covering a portion of the electrical connector 106 and a stop ring 204 in an annular groove 128 of the casing 126 to retain the connecting collar 108 thereon. The connecting collar 108 is capable of removably connecting the probe 100 to the port 326 of the sonde or other water quality monitoring device with a water-tight seal. The connecting collar 108 may be a threaded collar. The casing 126 may be or include a metal or metal alloy and/or an anti-biofouling material. In one embodiment, the casing 126 is the same material as the housing 119. Other water quality monitoring devices may include a data logger, a computer, a handheld monitoring unit, or any other device capable of connecting to the probe and communicating with the sensor therein to monitor the environment surrounding the sensor. The environment surrounding the turbidity head 102 of the probe 100 may be, but is not limited to, air, a gas, a vapor, water, and/or a test solution containing an analyte.

Still referring to FIGS. 1-2, the electrical connector 106 includes at least one male pin 122 and at least one female receptacle 124, and preferably the male pin and female receptacle are wet mateable connectors. In one embodiment, the electrical connector 106 may include a wet mateable connector having two male pins 122 and two female receptacles 124. The electrical connector 106 may also include electrical leads 129 coupling the electrical connector 106 to the circuit board 120. The leads 129 may be soldered to the circuit board 120 or may plug into a component on the circuit board 120, such as a female header, a card edge connector, a printed circuit board connector, a USB connector, or any other known or later-developed connector.

As shown in FIG. 2, the circuit board 120 connects the electrical connector 106 to the sensor or optical components in the turbidity head 102. The circuit board 120 may include a plurality of components, such as memory, capacitors, analog to digital converters, and any other components that are needed to operate the sensor, collect data, store the data, and/or send the data to a device connected to electrical connector 106. In one embodiment, the circuit board 120 may include a pressure sensor 190. The pressure sensor 190 provides one means for detecting a leak or a break in the water-tight housing 119. This sensor may be used to test probes 100 during manufacturing after welding the housing to the other components or in the field to test the probes before, during, and/or after monitoring an environment.

Figure 3:
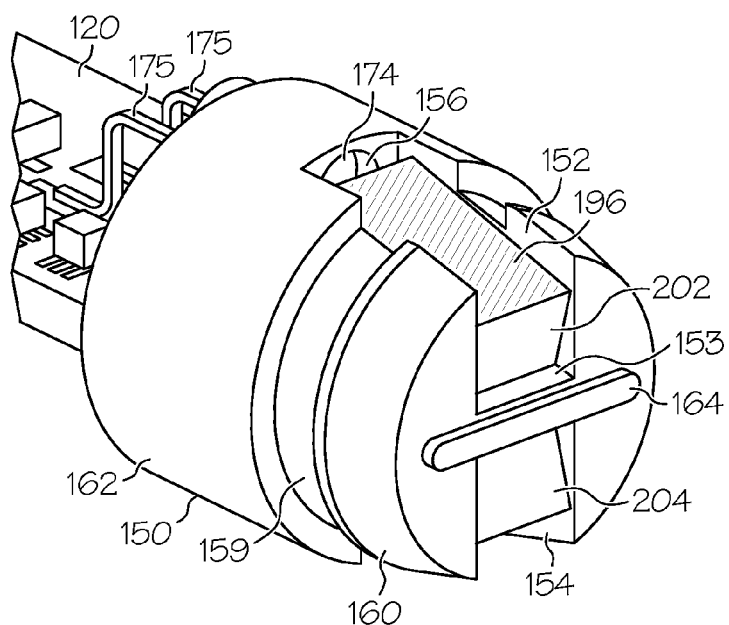
FIG. 3 is an end perspective view of the head of the turbidity probe of FIG. 1 with the cap removed.
Figure 4:
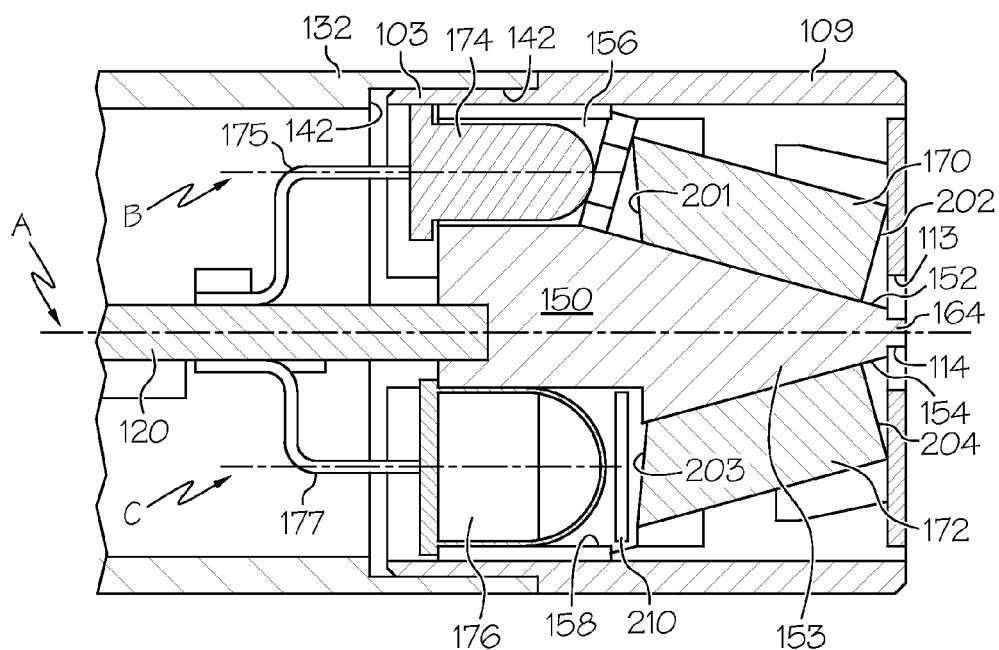
FIG. 4 is a side, cross-sectional view of the head of the turbidity probe of FIG. 2.

Referring now to FIGS. 2-4, the turbidity head 102 contains a sensor, in particular optical components, that have access to the environment surrounding the turbidity head to monitor at least one parameter of that environment. The optical components include a light source 174 providing an outgoing light ray 186, a photodetector 176 capable of detecting an incoming light ray 188, an isolator 153 separating the light source 174 from the photodetector 176, and a first reflector 170 in the path of either the outgoing light ray 186 or the incoming light ray 188, which may be part of or received in an optics receptacle 150. The first reflector 170 is positioned to reflect either the outgoing light ray 186 or the incoming light ray 188 to achieve a measurement angle α defined between the outgoing light ray 186 and the incoming light ray 188 of ninety degrees plus-or-minus two and a half degrees to comply with the standard ISO 7027 for turbidity measurement. The isolator 153 blocks the light from the light source's side of the turbidity head 102 from reaching the photodetector's side thereof, which if not blocked will cause a high background signal.

As shown in FIG. 4, the turbidity head 102 has a central longitudinal axis A that is coextensive with the central longitudinal axis of the probe 100. In one embodiment, the central longitudinal axis A may bisect the isolator 153 and divide the optics receptacle 150 into two halves, one-half housing the light source 174 and the second-half housing the photodetector 176. The light source 174 has a central longitudinal axis B and includes at least one lead 175 that is connectable to the circuit board 120. The photodetector 176 has a central longitudinal axis C and includes at least one lead 177 that is connectable to the circuit board 120. The leads 175, 177 may be soldered to the circuit board or may plug into a component of the circuit board such as a female header, a card edge connector, a printed circuit board connector, a USB connector, or any other known or later-developed connector.

For compact in-situ nephelometric turbidity sensors, because of dimensional limitation, conventional designs can hardly meet the ninety degree angle requirement of ISO 7027. The turbidity head 102 and probe 100 disclosed herein meet the ninety degrees (±2.5 degrees) by using at least one reflector 170, 172 to bend the outgoing light ray, or incident light, and/or the incoming scattered light ray to save space by enabling a more compact arrangement of the light source 174 and the photodetector 176. The at least one reflector of the present configuration enables the optical components to be packed into a housing having a maximum outer diameter of between about 13 mm to about 7 mm. As technology improves an even smaller housing may be possible.

Figure 6:
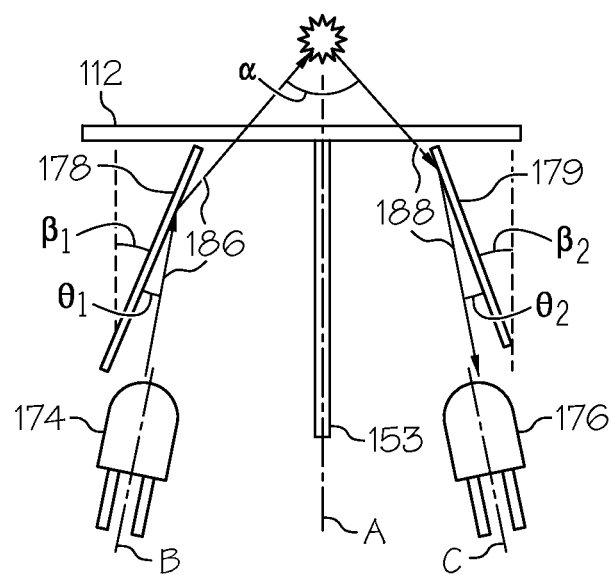
FIG. 6 is a side schematic view of another configuration of the components of a turbidity head.

The reflectors 170, 172 may be a prism, a reflective coating, a reflective film, and combinations thereof. In one embodiment, as shown in FIG. 3, the reflector is a prism having one total or partial reflective side 196, in particular, the exterior surface of side. The reflective side 196 may be reflective because of the presence of a reflective coating or a reflective film thereon. The reflective film may be adhered to the prism. In one embodiment, the prism includes a reflective coating on the exterior surface of side 196 that provides the prism with a mirrored surface. The prism may be a parallelepiped prism, but is not limited thereto. In one embodiment, the reflectors 170, 172 may be mirrors or as shown in FIG. 6 may be one or more reflective films 178, 179. The reflective films may be Mylar® PET reflective film or other metalized plastic film.

Figure 5:
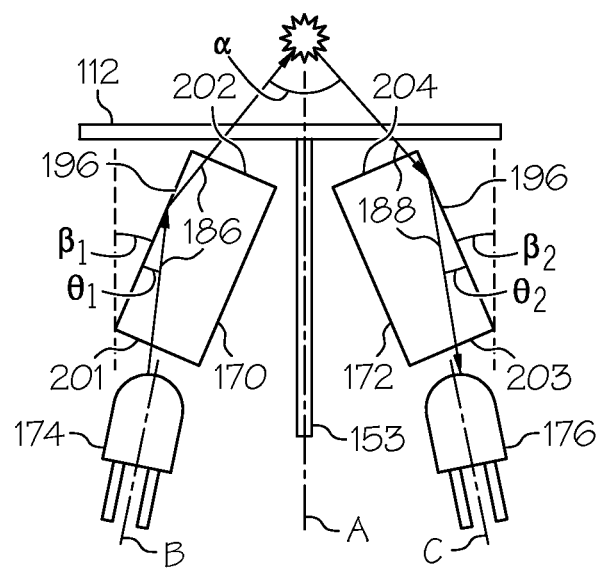
FIG. 5 is a side schematic view of one configuration of components of a turbidity head.

Regardless of which type of reflector or combinations of reflectors are present, to achieve the ninety degrees±2.5 degrees in a compact turbidity head 102, placement of the reflectors 170, 172 (or just one of the reflectors) is such that the tilt angles $\beta_1$, $\beta_2$ and the incident angles $\theta_1$, $\theta_2$, labeled in FIGS. 5-8, result in a measurement angle α that meets the ISO 7027 requirements. In one embodiment, the tilt angles $\beta_1$, $\beta_2$, can be between 0 to 45° such that the tilt of the reflector 170, 172 (or reflective films 178, 179 of FIG. 6) places the second end 202 or 204 of the reflector closer to the central longitudinal axis of the turbidity head 102 than the first end 201, 203 of the reflector. The first and second ends of the reflectors are shown in FIGS. 3-5. The light source 174 incident angle $\theta_1$ and the photodetector incident angle (detection angle) $\theta_2$ can be between 0 to 90°. In another embodiment, the tilt angles are between about 10° to about 30° or between about 15° to about 25° and the incident angles are between about 5° to about 90°.

To prevent total internal reflection of light reflecting from the reflectors 170, 172 (FIGS. 3-5) or reflective films 178, 179 (FIG. 6), the incident angle θ should be less than the critical angle, $$\theta < \arcsin(n_0/n_1).$$

Where $n_0$ is the ambient medium refractive index, it is typically air with refractive index of 1, and $n_1$ is the refractive index of the reflector, typically $n_1$ ranges from 1.48 of acrylic to 1.76 of sapphire glass.

Figure 7:
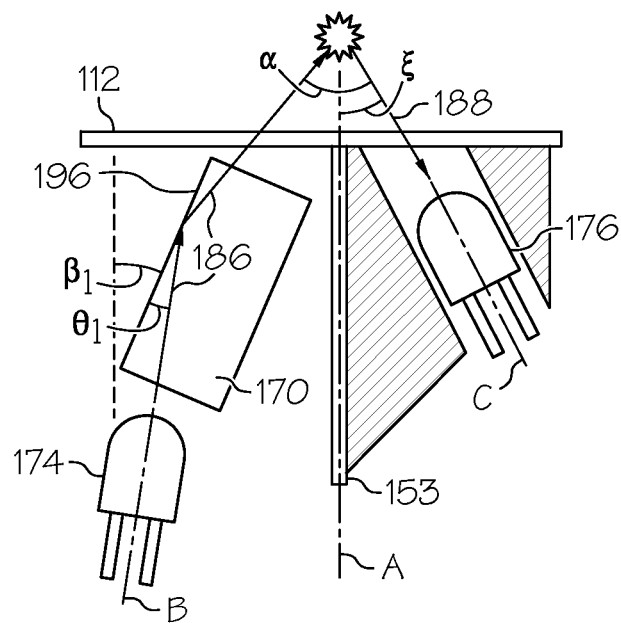
FIGS. 7 and 8 are side schematic views of alternate configurations for the components of the turbidity head.
Figure 8:
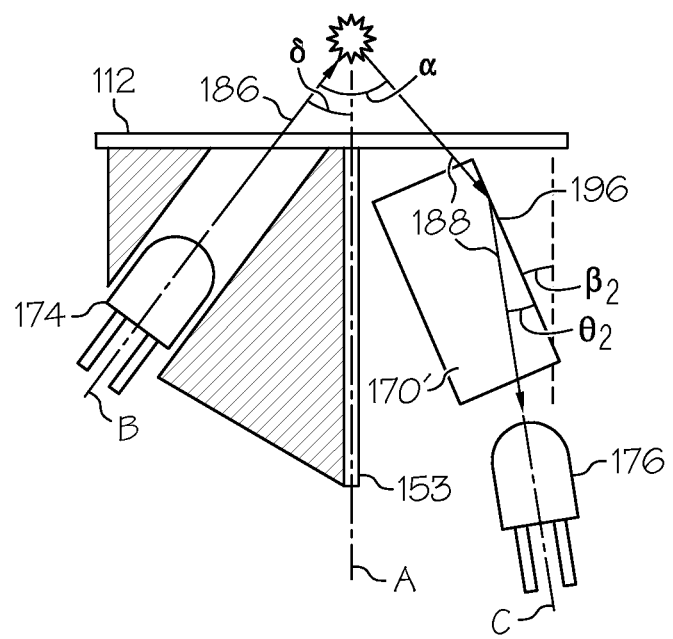

The tilt angles $\beta_1$, $\beta_2$ and the incident angles $\theta_1$, $\theta_2$ may be adjusted by altering the receptacles 152, 154, 156, and/or 158 in the optics receptacle 150 shown in FIGS. 3-4. The variations for the receptacles within the optics receptacle 150 include, but are not limited to: (1) receptacle 152, a first cradle, holds the first reflector 170 at a desired tilt angle $\theta_1$; but if not present, then the first cradle 152 holds the light source 174, as shown in FIG. 8, at a desired orientation angle $\delta$ measured as the angle the central longitudinal axis of the light source, axis B, makes to the central longitudinal axis A of the probe 100; (2) receptacle 154 (FIGS. 3-4), a second cradle, holds the second reflector 172 at a desired tilt angle $\beta_2$; but if not present, then the second cradle 154 holds the photodetector 176, as shown in FIG. 7, at a desired orientation angle E measured as the angle the central longitudinal axis of the photodetector, axis C, makes to the central longitudinal axis A of the probe; (3) receptacle 156, a light source receptacle, (FIG. 4) holds the light source 174 at a selected incident angle $\theta_1$ as shown in FIGS. 5-7 when the first reflector 170 is present; and (4) receptacle 158, a photodetector receptacle, (FIG. 4) holds a photodetector 176 at an incident angle $\theta_2$ as shown in FIGS. 5-6 when the second reflector 172 is present.

The orientation angles $\delta$ or $\epsilon$ may be such that the central longitudinal axis of the light source 174 or the photodetector 176 makes about a 5° to about a 60° angle to the central longitudinal axis A of the probe. In one embodiment, the orientation angle $\delta$ is about a 45° angle to the central longitudinal axis A of the probe. In another embodiment, the orientation angle $\epsilon$ is about a 45° angle to the central longitudinal axis A of the probe In the embodiment of FIGS. 3-5, the reflectors 170, 172 are parallelepiped prisms. The first end 201 of the first parallelepiped reflector 170 receives the outgoing light ray 186 from the light source 174 and the second end 202 receives the reflected outgoing light ray, which exits therethrough into the environment surrounding the turbidity head 102. The second parallelepiped reflector 172 has a first end 203 and a second end 204 positioned such that the second end 204 receives the incoming light ray 188 from the environment and the first end 203 receives the reflected incoming light ray, which exits the first end 203 to reach the photodetector 176. To minimize the scattering loss of light at the first and second ends 201, 202 and 203, 204 of the first and second parallelepiped reflectors 170, 172, respectively, the first and second ends are polished to optical quality.

In the embodiments of FIGS. 3-5 and 7-8, the reflectors 170, 172 are parallelepipeds having a reflective surface 196. As shown in FIGS. 5-7, light 186 emitted from the light source 174 is reflected from a mirrored or reflective surface 196 of a first rectangular prism 170 (FIGS. 5 and 7) or a first reflective film 178 (FIG. 6) and then transmits through optical aperture 112. Similarly, as shown in FIGS. 5-6 and 8, when a second rectangular prism 172 or a second reflective film 178 is present, the incoming (scattering) light ray 188 is reflected from a mirrored surface or reflective surface 196 and transmits the incoming light ray 188 to the photodetector 176. In any of these embodiments, whichever or both of the light source 174 or the photodetector 176 that are in the path of a reflector 170, 172, 178, 179 is positioned such that its central longitudinal axis B and C are generally parallel to the central longitudinal axis A of the turbidity head 102. As used herein, "generally parallel" means that the central longitudinal axis B of the light source 174 and/or the central longitudinal axis C of the photodetector 176 form an angle with the central longitudinal axis A of the turbidity head 102 of about 20° or less and more preferably about 10° or less.

In one embodiment, the light source 174, best seen in FIG. 4, is a light emitting diode. In another embodiment, the light source 174 may be a laser diode, a VCSEL, a fiber source or a miniature lamp.

In one embodiment, the photodetector 176, best seen in FIG. 4, is a photodiode. In another embodiment, the photodetector 176 may be a PIN diode, an avalanche photodiode, a CMOS photodiode or a photosensitive electron tube.

In one embodiment, as shown in FIG. 4, the turbidity head 102 may include an optical filter 210 in the path of the incoming ray, which includes the photodetector 176. The optical filter 210 may be positioned adjacent to the photodetector 176 and may be between the photodetector 176 and the reflector 172, if present. The optical filter 210 helps prevent scattered or other unwanted light from reaching the photodetector 176. In one embodiment, the optical filter is an absorptive filter. In another embodiment, the optical filter may be an interference filter or metal mesh optical filter.

As shown in FIGS. 1-2 and 4, the turbidity head 102 includes a cap 109 covering the optics receptacle 150 housing the optical components. The cap 109 includes a generally closed end, optical aperture 112, and a generally cylindrical hollow body that is configured to receive the optics receptacle 150. The cap 109 includes a neck 103 that has a smaller outer diameter than the remainder of the cap 109 and defines an annular seat for receiving the first end 132 of the housing 119. The neck 103 may be positioned adjacent the first end 132 of the housing 119 of the probe body 104 (best seen in FIG. 4) to form a water-tight seal.

The optical aperture 112, best seen in FIG. 1, may include a window 113 and a slot 114 therein. The window 113 and the slot 114 may bisect one another such that together they generally resemble a "plus sign" (+). The window 113 and slot 114 may be generally centrally positioned within the optical aperture 112. The window 113, however, should be aligned with the first and second reflectors 170, 172 if present, and if not present, then the window 113 should be aligned with the light source 174 or the photodetector 176. The slot 114 is configured such that it receives a tab 164 that is integral with or connected to the optics receptacle 150, in particular, with the isolator 153. The tab 164 aides in placing the isolator in the best position to keep light from the light source half of the optics receptacle 150 separated from the photodetector half and separates the window 113 into a light source window 113$a$ and a photodetector window 113$b$.

The cap 109 may be a metal or metal alloy and/or an anti-biofouling material. The metal or metal alloy may be water resistant and corrosive resistant. Suitable materials include titanium, stainless steel, nickel, copper, graphite, and alloys thereof. In one embodiment, the cap 109 is titanium. In another embodiment, the cap 109 is an antifouling copper-nickle alloy with a high copper content. For example, the antifouling copper-nickle alloy may be a 90-10 CuNi alloy or a 70-30 CuNi alloy.

In another embodiment, the cap 109 may be an antifouling plastic, for example, a polyethylene, polypropylene, or nylon that may include an anti-fouling compound such as capsaicin, capsicum, furan compounds, copper compounds, lactones, alkyl-phenols, organotin compounds, antibiotics, or mixtures thereof. The plastic material may be a suitable engineering thermoplastic material with good material strength that lends itself to having a window, slots, and/or annular grooves or other features of the sensor or turbidity head formed therein. The thermoplastic may be water, corrosion, and/or chemically resistant, and electrically insulating. A water-tight bond between the cap 109 and the housing 119 of the probe body is important since the probe 100 is often used under water at significant depths and experiences increased pressure as it descends. If a gap occurs, water may be able to enter the probe head and damage its components.

The thermoplastic material may be an acetal, acrylic, acrylonitrile-butadiene-styrene terpolymer, a polyamide, a polycarbonate, a polyetherimide, a polyphenylene ether, a polyphenylene sulfide, a polysulfone, polyvinyl alcohol, or a thermoplastic polyester. In one embodiment, the thermoplastic material is an imide, preferably a non-filled imide such as a polyetherimide. Polyetherimides are commercially available under the brand name Ultem® available from SABIC Innovative Plastics.

The turbidity head 102 may also include one or more leads 175, 177 (FIGS. 2, 4) extending from the optics receptacle 150 for connection to the circuit board 120. The leads may be soldered directly to the circuit board 120 or may plug into a component on the circuit board 120, such as a female header, a card edge connector, a printed circuit board connector, a USB connector, or any other known or later-developed connector.

In order to understand the method of assembly of the probes 100, additional detail about housing 119 is needed. As best seen in FIG. 2, the housing 119 is a hollow, generally cylindrical tube having a distal end 132 defining a first open end and a proximal end 134 defining a second open end. The inner diameter of the housing 119, overall, is larger that the circuit board 120 so that the housing 119 slides easily over the circuit board 120 with enough clearance to avoid bumping the circuit board 120 on the housing 119 and possibly damaging the circuit board 120 or one of its components. The housing 119 has a substantially uniform outer diameter, but has a plurality of different inner diameters. As shown in FIG. 4, the interior of the housing 119 has an annular lip 142 indented into the inner wall of the housing 119 just interior to the open distal end 132 and, as shown in FIG. 2, an enlarged opening 146 indented into the inner wall of the housing 119 just interior to the open proximal end 134. A chamber 144 is located between the annular lip 142 and enlarged opening 146 of the housing 119. The housing 119 may be or include a metal or metal alloy and/or an anti-biofouling material such as those discussed above with respect to the cap 109.

The annular lip 142 has a larger inner diameter than the chamber 144 and extends generally uniformly into the interior of the housing 119 and is contiguous with the open distal end 132 thereof. The annular lip 142 is proportional in width or diameter to the width or outer diameter of the neck 103 of the cap 109, so that the end of neck 103 seats on the annular lip 142 and the open distal end 133 seats against the annular seat 116 of the cap 109.

The enlarged opening 146 at the proximal end 134 of the housing 119 extends generally uniformly into the interior of the housing 119 and is contiguous with the open proximal end 134. The enlarged opening 146 has a larger inner diameter compared to the chamber 144 and may have a larger inner diameter compared to the annular lip 142. The enlarged opening 146 provides the advantage of receiving the reducing ring 148, which increases the surface area for connecting the housing 119 to the electrical connector 106, in particular to the casing 126 on the electrical connector 106. The increased surface area provides for a stronger bond, in particular, for a stronger weld joint between the components and an improved water-tight seal.

Figure 10:
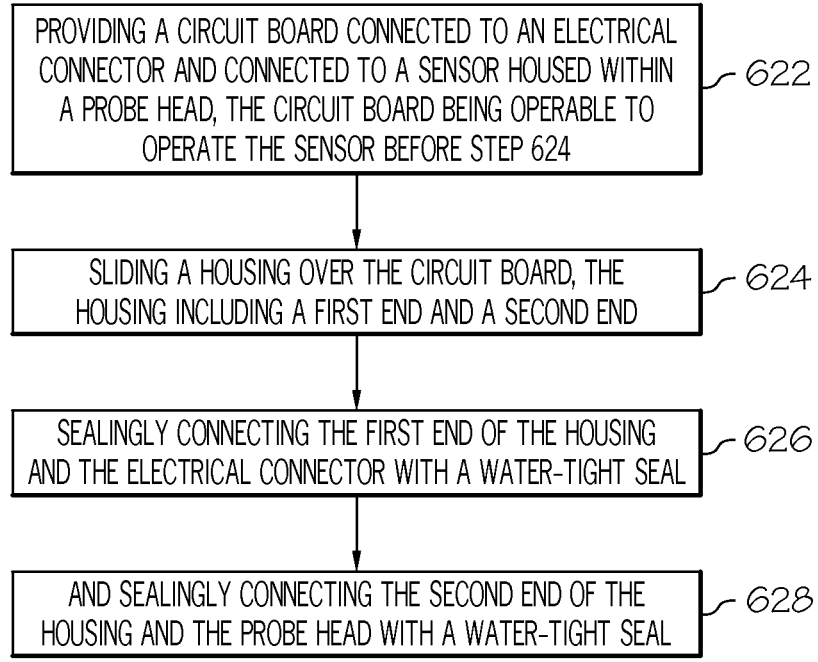
FIG. 10 is a diagram of one embodiment of a process of assembling a probe that is similar to the probe of FIG. 1.

The probes 100 may be assembled using the process of FIG. 10. The process includes the step 622 of providing a circuit board 120 connected to an electrical connector 106 and connected to a sensor or optical components housed within the turbidity head 102. The process includes the step 624 of sliding a housing 119 having a first end and a second end over the circuit board 120, the step 626 of sealingly connecting the first end of the housing 119 and the first electrical connector 106 with a water-tight seal, and the step 628 of sealingly connecting the second end of the housing 119 and the probe head 102 with a water-tight seal. The circuit board 120 is operable to operate the sensor or optical components and is preferably operable before sliding the housing 119 over the circuit board 120. When assembled, the probe 100 can monitor parameters of an environment, typically an environment surrounding the turbidity head 102.

The step 626 of sealingly connecting the first end of the housing 119 and the first electrical connector 106 may include welding the two components together. Similarly, the step 628 of sealingly connecting the second end of the housing 119 and the turbidity head may include welding the two components together. The welding may be by any known technique, preferably a technique that can form a water-tight seal between the components and will not damage any of the parts of the probe, in particular, the circuit board. The welding may be arc, MIG, TIG, laser, electron beam, resistance, ultrasonic, or plasma welding procedures. Some welding techniques may provide too much heat for the close proximity of the weld to the circuit board. Preferably, the welding is laser welding.

Laser welding is a non-contact process requiring access to the weld zone from only one side of the parts being welded. The weld is formed as the intense laser light rapidly heats the material, typically only taking milliseconds. One advantage that laser welding offers is the minimal amount of heat that is added during processing. This advantage makes laser welding ideal for thin sections or products that require welding near electronics. Low heat input, combined with an optical (not electrical) process, also means greater flexibility in tooling design and materials. Another advantage of laser welding is that filler material is generally not added.

Whether it is through part design, tooling design, or a combination of both, one factor for a successful laser weld is that components be held in intimate contact along the weld area. The ideal weld joint should have no gap between components. This is especially true in a lap weld joint configuration. Even the slightest space between parts can be the difference between a consistently strong weld, and no weld at all. Butt or seam weld joints are slightly more tolerant. Since laser welding is most often done without the benefit of filler metal, the material that forms the fillet must be "drawn" from the sections being welded.

Step 628 is preferably accomplished using laser welding. The neck 103 of the turbidity head 102 may define an annular seat 116 for the second end 131 of the housing 119, such that laser welding the two components together includes welding the second end 131, in particular annular lip 142, of the housing 119 to the neck 103.

In another embodiment, the process includes the step of providing a reducing ring 148 and sealingly connecting, preferably by laser welding, the reducing ring 148 to the open proximal end 134 of the hollow housing 119. The step of sealingly connecting the reducing ring 148 to the housing 119 preferably occurs before the step 624 of inserting the circuit board 120. Thereafter, the step 626 of sealingly connecting the open proximal end 134 includes welding, preferably by laser welding, the reducing ring 148 to the casing 126 of the electrical connector 106. The reducing ring 148 is designed to fill the gap between the enlarged opening 146 of the open proximal end 134 of the housing 119 and the electrical connector 106 for a stronger weld. The reducing ring 148 also provides additional material to form the "fillet" of the weld.

In one embodiment, the housing 119 is slid over the circuit board 120 by sliding the distal end 132 over the electrical connector 106 and into engagement with the turbidity head 102. In another embodiment, the housing 119 is slid over the circuit board starting at the turbidity head 102 before the cap 109 is slid over the optics receptacle 150.

Once the process is complete, a probe 100, for example, similar to that illustrated in FIG. 1 is formed that has a first weld 180 between the reducing ring 148 and the proximal end 134 of the housing 119, a second weld 182 between the neck 103 of the probe head 102 and the distal end 132 of the housing 119, and a third weld 184 between the reducing ring 148 and the casing 126 of the electrical connector 106. The reducing ring 148 is inserted into the enlarged opening 146 to provide a larger surface area for welding, to reduce the gap between components, and provide additional material for the placement of the first weld 180. The end of the casing 126 may include a thickened portion that is reinforced with additional material for an enhanced weld and/or to protect the electrical connector 106 underneath from exposure to the heat from the welding process.

The circuit board 120 is connected to the electrical connector 106, and the turbidity head 102 is preferably, and advantageously, an operable unit prior to being inserted into the housing 119. An operable unit includes the capability to operate the sensor, test the functions of the sensor and/or the circuit board, calibrate the sensor, and/or program the circuit board. Accordingly, the process may include the additional steps of testing the circuit board 120 to determine that the sensor is functioning and/or calibrating the sensor before inserting the circuit board 120 into the housing 119.

The process may also include the step of connecting the probe head 102 to the first end 130 of the circuit board 120, which may include soldering the leads 175, 177 from the turbidity head 102 to the circuit board 120. In another embodiment, the step of connecting the turbidity head 102 may include plugging the turbidity head 102 into a connector on the first end 130 of the circuit board 120, such as a female header, a card edge connector, a printed circuit board connector, a USB connector, or any other known or later-developed connector.

The process may also include the step of connecting the electrical connector 106 to the second end 131 of the circuit board 120. Like the turbidity head 102, the connecting of the electrical connector 106 may include soldering leads 129 to the circuit board 120 or plugging the leads into a connector on the second end 131 of the circuit board 120, such as those discussed above.

In another embodiment, the probe 100 may be mounted within a multi-probe assembly, for example, a sonde 300 shown in FIG. 9, like the sonde described in U.S. Pat. No. 6,779,383 modified to include the turbidity probe 100 disclosed herein or other probes disclosed in Applicants' related patent applications that have various sensing capabilities. The multi-probe assembly may include a wiper having a wiper element or an arm with a brush or other cleaning element that cleans, not only the disclosed turbidity probe 100, but other sensors in other probes. For example, the sonde 300 may include a turbidity probe 100 similar to those disclosed herein, a dissolved oxygen sensor 312, a temperature-conductivity sensor 316, and a sensor 318, which can be a chlorophyll or Rhodamine sensor. The sonde 300 may also include a sensor 310 or a sensor-less probe having a wiper element and/or an arm 322 having a cleaning element 320 extending therefrom beyond the diameter of the sensor. The cleaning element 324 may be a brush, foam material, sponge, wiper, or other material capable of cleaning the sensors.

It will be appreciated that while the invention has been described in detail and with reference to specific embodiments, numerous modifications and variations are possible without departing from the spirit and scope of the invention as defined by the following claims.

What is claimed is:

1. A turbidity head for a turbidity sensor or probe comprising:
    a light source providing an outgoing light ray toward a fluid sample;
    a detector capable of detecting an incoming light ray reflected from the fluid sample;
    an isolator separating the light source from the detector portion; and
    a first reflector in the path of either the outgoing light ray or the incoming light ray;
    wherein the first reflector is positioned to reflect either the outgoing light ray or the incoming light ray to achieve a measurement angle defined between the outgoing light ray and the incoming light ray of ninety degrees plus-or-minus two and a half degrees.

2. The turbidity head of claim 1, wherein the first reflector is positioned at a tilt angle between 0° to 45°.

3. The turbidity head of claim 2 wherein the first reflector is positioned at a tilt angle between about 10° to about 30°.

4. The turbidity head of claim 1, wherein the first reflector includes a prism, a reflective film, a reflective coating, and combinations thereof.

5. The turbidity head of claim 4, wherein the first reflector is a prism having one reflective side.

6. The turbidity head of claim 5, wherein the first reflector is positioned to reflect the outgoing light ray and a second reflector is positioned to reflect the incoming light ray.

7. The turbidity head of claim 5, wherein the reflective side includes the reflective coating or the reflective film thereon.

8. The turbidity head of claim 1, wherein the first reflector is positioned such that the incident angle is less than the critical angle.

9. The turbidity head of claim 1, wherein the turbidity head has a central longitudinal axis and whichever of the light source or the photo detector is in the path of the first reflector has a central longitudinal axis that is generally parallel to the central longitudinal axis of the turbidity head.

10. The turbidity head of claim 9, wherein the reflector is a parallelepiped prism, the prism being positioned at a tilt angle between 0° to 45° that places the second end of the prism closer to the central longitudinal axis of the turbidity head than the first end of the prism.

11. The turbidity head of claim 1, further comprising a housing having a maximum diameter of about 13 mm, the housing enclosing the light source, the photodetector, the isolator, and the first reflector.

12. The turbidity head of claim 11, wherein the housing is a cap having a closed end that includes an optics aperture.

13. The turbidity head of claim 4, wherein the first reflector is a reflective film.

14. The turbidity head of claim 13, wherein the first reflector is positioned to reflect the outgoing light ray and a second reflector is positioned to reflect the incoming light ray.

15. The turbidity head of claim 1, wherein the turbidity head has a central longitudinal axis and whichever of the light source or the photo detector that does not include the reflector has a central longitudinal axis that is oriented at about a 5° to about a 60° angle to the central longitudinal axis of the turbidity head.

16. A turbidity sensor comprising:
    a watertight housing that houses a light source providing an outgoing light ray toward a fluid sample, a detector capable of detecting an incoming light ray reflected from the fluid sample, an isolator separating the light source from the detector portion, a first reflector in the path of either the outgoing light ray or the incoming light ray, and a circuit board electrically coupled to the light source and the detector;

wherein the first reflector is positioned to reflect either the outgoing light ray or the incoming light ray to achieve a measurement angle defined between the outgoing light ray and the incoming light ray of ninety degrees plus-or-minus two and a half degrees.

17. The turbidity sensor of claim 16, further comprising an electrical connector electrically coupled to the circuit board, the electrical connector being capable of electrically coupling the circuit board to a water monitoring device.

18. The turbidity sensor of claim 17, wherein the electrical connector is a wet mateable connector.

19. The turbidity sensor of claim 16, wherein the water tight housing includes a cap that covers an optics receptacle that receives the light source, the photodetector, and the reflector.

20. The turbidity sensor of claim 16, further comprising a second reflector, wherein the first reflector is positioned to reflect the outgoing light ray and the second reflector is positioned to reflect the incoming light ray.

* * * * *